United States Patent [19]

Bomardelli et al.

[11] Patent Number: 4,870,179

[45] Date of Patent: Sep. 26, 1989

[54] PROCESS FOR PREPARING LYSERGOL DERIVATIVES

[75] Inventors: Ezio Bomardelli; Giuseppe Mustich, both of Milan, Italy

[73] Assignee: Inverni Della Beffa SpA, Milan, Italy

[21] Appl. No.: 763,430

[22] Filed: Aug. 7, 1985

[30] Foreign Application Priority Data

Aug. 7, 1984 [IT] Italy ................. 22245 A/84

[51] Int. Cl.$^4$ ............................. C07D 457/04
[52] U.S. Cl. ......................... 546/67; 204/157.71
[58] Field of Search ............. 546/67, 68, 69, 65; 204/158

[56] References Cited

U.S. PATENT DOCUMENTS

| 3,228,943 | 1/1906 | Bernardi et al. | 546/68 |
| 3,585,201 | 6/1971 | Arcamone | 544/346 |
| 3,647,655 | 3/1972 | Bernardi et al. | 546/69 |
| 3,879,554 | 4/1975 | Temperilli | 546/68 |
| 4,232,157 | 11/1980 | Enrico | 546/68 |

FOREIGN PATENT DOCUMENTS 4664 10/1979 European Pat. Off. .
156645 10/1985 European Pat. Off. .

*Primary Examiner*—Cecilia Shen
*Attorney, Agent, or Firm*—Browdy and Neimark

[57] ABSTRACT

A method of preparing lysergol derivatives, particularly 10α-methoxy lumilysergol, 1-methyl-10α-methoxy-lumilysergol and C8 esters of 1-methyl-10α-methoxy-lumilysergol, is provided characterized in that lysergol esters are subjected to photo-chemical reaction in methanol/sulphuric acid to form esters of 10α-methoxy lumilysergol. The esters can be subsequently hydrolyzed to obtain 10α-methoxy-lumilysergol, or can be transesterified with salts of other acids and/or N-methylated.

11 Claims, No Drawings

PROCESS FOR PREPARING LYSERGOL DERIVATIVES

The invention relates to a method of preparing lysergol derivatives, particularly 10α-methoxy-lumilysergol, 1-methyl-10α-methoxy-lumilysergol and esters thereof having the formula (I)

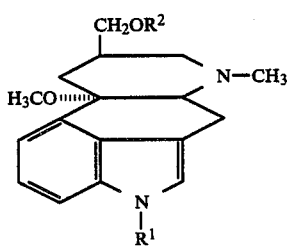

where $R^1$ denotes hydrogen or methyl and $-OR^2$ represents a free or esterified hydroxy group. For example, the moiety $R^2$ can denote hydrogen, or an alkane or arene-sulphonyl or an R—CO radical where R stands for alkyl, aryl or alkaryl, which may be unsubstituted or substituted by halogen if required.

Compounds of formula (I) in which $R^1$ and $R^2$ are hydrogen or $R^1$ is methyl and $R^2$ is hydrogen, are known and their preparation is described in the literature, e.g. in Italian patent application No. 22011 A/78. However the various methods previously proposed are unsatisfactory either with regard to the total reaction yield or the purity of the products or for both reasons.

For example, a description has been given of the photo-chemical reaction of lysergol in methanol/sulphuric acid and subsequent methylation of the indolic nitrogen of the thus-obtained 10α-methoxylumilysergol, with methyl iodide in the presence of KOH and in dimethyl sulphoxide in accordance with Reaction Scheme A Reaction Scheme A

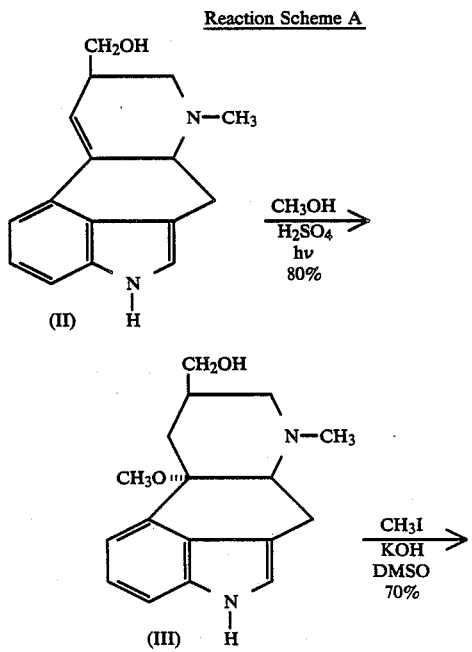

-continued
Reaction Scheme A

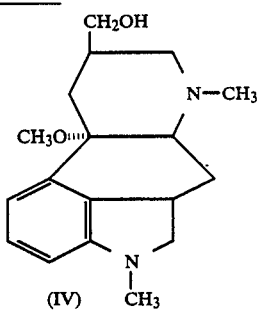

The yield from the first step is 80% whereas the transition from (III) to (IV) occurs with a 70% yield, so that the total yield of 1-methyl-10α-methoxy-lumilysergol is only 56%.

According to another method described and claimed by the present applicants in Italian Patent Application No. 20242 A/84 (European Patent Application No. 85302101.2), lysergol esters are alkylated on the indolic nitrogen with methyl iodide and potassium in liquid ammonia, followed by photo-chemical addition of methanol in sulphuric acid and subsequent hydrolysis of the ester group. The product, 1-methyl-10-α-methoxy lumilysergol (IV), is obtained in a greater yield than that of the first method, but a rather laborious purification is required in one or more stages of the process.

It has now been found possible to obtain 10α-methoxy-lumilysergol of high purity and in a yield equal to or greater than 94% if the photo-chemical reaction is carried out in methanol/sulphuric acid under very specific reaction conditions given hereinafter, not using lysergol as such as starting material but an ester thereof (most preferably the 8-methane sulphonyl derivative).

It is unexpectedly been found that the reaction, performed on esters which are stable under the reaction conditions, occurs in the substantial absence of by-products such as ethers, or of elimination reactions involving the alcohol group. This is achieved, according to the invention, by irradiating lysergol esters in methanol at low temperature, preferably between $-10°$ and $-30°$ C., under controlled acidity conditions, with UV light of wavelength from 300 to 370 nm, preferably at 330 nm. When the addition of methanol is complete, it is only necessary to bring the reaction mixture back to room temperature to deacylate the ester group and obtain a substantially quantitative yield of 10α-methoxy-lumilysergol (III).

The process according to the invention can also be used to isolate the 10α-methoxy esters obtained by the procedure described (preferably the methane sulphonic ester) and subject them to N-alkylation in liquid ammonia, obtaining the corresponding esters of 1-methyl-10α-methoxy-lumilysergol (Ia). These esters, finally, can be transesterified to esters (Ib) of 1-methyl-10α-lumilysergol having special therapeutic importance.

Thus according to the present invention there is provided a method of preparing a lysergol derivative of formula (I)

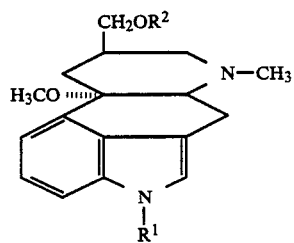

(I)

in which R¹ represents hydrogen or methyl, and —OR² represents a free or esterified hydroxyl group characterised in that a lysergol ester of formula (VII)

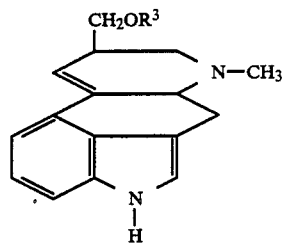

(VII)

in which —OR³ represents an esterified hydroxyl group, is subjected to photo-chemical reaction at a temperature below 0° C. in methanol containing not more than 10% (w/v) of $H_2SO_4$ to produce an ester of 10α-methoxy lumilysergol of formula (VIII)

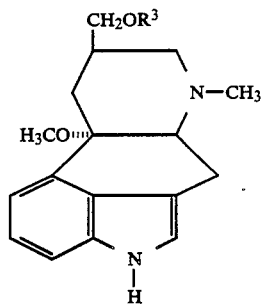

(VIII)

and the resulting ester of 10α-methoxy lumilysergol of formula (VIII) is converted to a compound of formula (I) by one or more of the following optional steps carried out in any appropriate order:

(a) N-methylation;
(b) hydrolysis to form a compound in which OR² represents hydroxyl;
(c) esterification of a compound in which OR² represents hydroxyl to form a compound in which OR² represents an esterified hydroxyl group;
(d) transesterification of a compound in which OR² represents an esterified hydroxyl group.

Preferably the photochemical reaction is carried out in methanol containing from 2 to 10% (w/v) of $H_2SO_4$, most preferably 3% w/v. (The expression "x% (w/v)" means x grams/100 mls).

The reactions according to the invention in its preferred embodiments can be summarised in the following Reaction Scheme B.

Reaction Scheme B

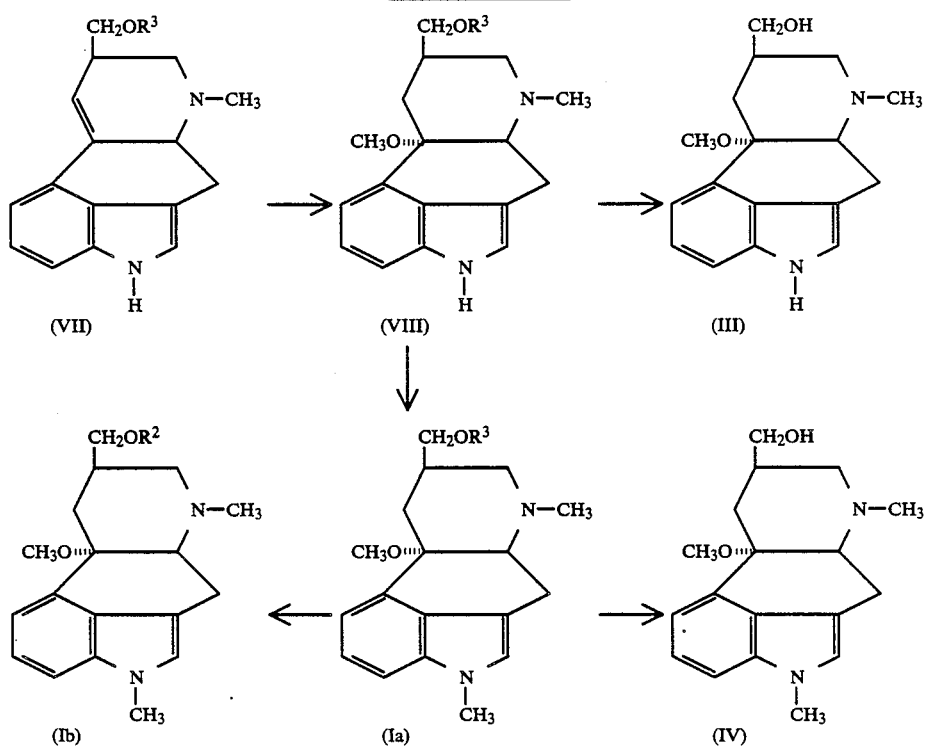

In the above Reaction Scheme, R² and R³ are as defined above, but preferably R³ represents a lower alkanoyl radical, most preferably formyl, acetyl, or an alkane sulphonyl or arene sulphonyl radical such as benzene sulphonyl, p-toluene sulphonyl or preferably methane sulphonyl. $R^2$ represents an acyl radical different from $R^3$, preferably a 5-bromopyridine-3-carbonyl radical. The preference given to acetyl, methane sulphonyl, tosyl and similar alkane or arene sulphonyl radicals as $R^3$ stems from the fact that these radicals are good leaving groups, more particularly with a view to transesterifying compounds (Ia) with suitable carboxylates to obtain esters (Ib).

Alkyl and alkanyl groups referred to herein are preferably lower alkyl and lower alkanoyl groups, by which is meant such groups containing up to 4 carbon atoms.

The initial lysergol esters of formula (VII) can be prepared by known methods, e.g. by reacting lysergol of natural origin with carboxylic or sulphonic acid chlorides in pyridine or by other conventional reactions.

The photo-chemical reaction for conerting (VII) to (VIII) is performed in methanol/sulphuric acid with a concentration of acid not above 10% w/v, at temperatures below 0° C., preferably between −10° C. and −30° C. The subsequent N-methylation is preferably carried out by contacting a compound of formula (VIII) with an alkyl halide, preferably an alkyl iodide such as methyl iodide in liquid ammonia in the presence of sodium or potassium amides produced in the same reaction medium.

Finally, the transesterification reactions are conveniently performed in aprotic solvents such as dimethyl formamide or dimethyl sulphoxide, with salts of the acids from which it is desired to obtain the corresponding esters.

The following examples illustrate the invention without limiting it in any way.

EXAMPLE 1

10-methoxy-lumilysergol 10 g of lysergol 8-methane sulphonate were dissolved in 250 ml of a mixture of 3% w/v of concentrated sulphuric acid in methanol previously cooled to −30° C. The solution, kept at a temperature of −20° C. and under nitrogen, was irradiated by a UV lamp emitting at 330 nm for about 2 hours. When the reaction was complete, the reaction mixture was diluted with 250 ml of water, made alkaline with NaOH to pH 8.5 and extracted with 3×150 ml of methylene chloride. The organic phase containing 10α-methoxylumilysergol methanesulphonate was concentrated to dryness in vacuo and the residue was taken up with 100 ml of anhydrous dimethylformamide and 5 g of potassium acetate. After keeping at 50° C. for 4 hours under nitrogen, the reaction mixture was cooled at room temperature and 20 ml of 10% potassium hydroxide in methanol were added. After 1 hour 500 ml of 5% aqueous NaCl were added and the precipitated product was isolated by filtration and dried. After crystallization from acetonitrile, 8 g of of pure 10α-methoxy-lumilysergol having the following chemical and physical characteristics were obtained:

m.p: 180°–182° C.; $[\alpha]_D^{20}$ (methanol)=+8.95; M+: 286.

EXAMPLE 2

10α-methoxy-lumilysergol 2.96 g of lysergol 8-acetate were dissolved in 100 ml of a mixture of 4.5% w/v of concentrated sulphuric acid in methanol previously cooled to −30° C. The solution, kept at a temperature of −20° C. and under nitrogen, was irradiated by a UV lamp emitting at 330 nm for about 2 hours. When the reaction was complete, the cooling was stopped and the solution was slowly brought to a temperature of +30° C., which was maintained for 3 hours. The reaction mixture was diluted with 150 ml of water and made alkaline with NH4OH to pH 8.5.

The hydromethanolic solution was extracted six times with 50 ml of methylene chloride. The organic phase, after dehydration over $Na_2SO_4$, was concentrated to dryness in vacuo and the residue was crystallized from methanol. The product was 2.75 g of pure 10α-methoxylumilysergol having the following chemical and physical characteristics:

m.p.: 180°–182° C.; $[\alpha]_D^{20}$ (methanol)=+8.95; M+: 286.

EXAMPLE 3

1-methyl-10α-methoxy-lumilysergol 8-methane sulphonate (a) 10 g of lysergol 8-methane sulphonate was irradiated as described in Example 1, and after 2 hours of irradiation, while always maintaining the temperature of about −20° C., 250 g of ice was added and the mixture was brought to pH 8.5 with NH4OH. The resulting solution was extracted with 6×100 ml of $CH_2Cl_2$; the combined extracts were dried over $Na_2SO_4$ and concentrated to dryness.

The product was 8.5 g of 10-methoxy lumilysergol 8-methane sulphonate, sufficiently pure for the subsequent reactions. (b) 0.78 g of metallic potassium and 0.04 g ferric nitrate were dissolved in 250 ml of liquid ammonia a multi-necked 500 ml flask cooled to −60° C. When dissolution was complete, 3.5 g of 10-methoxy lumilysergol 8-methane sulphonate and 1.45 g of methyl iodide were added. The reaction was kept at the same temperature for 3 hours, after which 1.5 g of ammonium chloride were added and distillation of ammonia began. The residue was dissolved in 20 ml cold methanol containing 1% acetic acid and the solution was diluted with 25 ml $H_2O$. The resulting solution was made alkaline at pH 8.5 and extracted twice with 20 ml of methylene chloride.

The chlorinated extracts were concentrated to dryness and the residue was recrystallized from acetonitrile, obtaining 3.3 g of pure product.

EXAMPLE 4

1-methyl-10α-methoxy-lumilysergol 8-(5-bromo-nicotinate)

3.85 g of 1-methyl-10α-methoxy lumilysergol 8-methane sulphonate, obtained as in Example 2, was dissolved in 20 ml of dimethyl formamide; 5 g of potassium 5-bromonicotinate were added to the solution and the mixture was kept under agitation at 40° C. for 4 hours. The solution was poured on to crushed ice, giving a suspension which was extracted with methylene chloride. The organic phase, carefully washed with water so as to eliminate dimethyl formamide, was concentrated to reduce the volume and the product was recrystallized from ether. The product was 4.7 g of 1-methyl-10α-methoxy lumilysergol 8-(5-bromonicotinate) having the following characteristics:

m.p: 138°–139° C. $[\alpha]_D^{20}$ =−20 (c=1, Py); +20 (c=5, $CHCl_3$)

We claim:

1. A method of preparing a compound of formula (I)

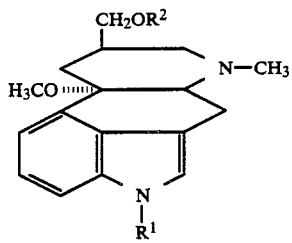

in which $R^1$ represents hydrogen or methyl, and —$OR^3$ represents a free or esterified hydroxyl group characterised in that a lysergol ester of formula (VII)

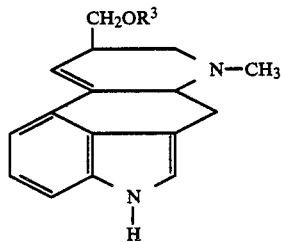

in which —$OR^3$ represents an esterified hydroxyl group is subjected to photo-chemical reaction at a temperature below 0° C. in methanol containing not more than 10% (w/v) of $H_2SO_4$ to produce an ester of 10α-methoxy lumilysergol of formula (VIII)

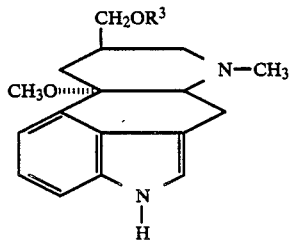

and the resulting ester of 10α-methoxy lumilysergol of formula (VIII) is converted to a compound of formula (I) by one or more of the following optional steps carried out in any appropriate order:
(a) N-methylation;
(b) hydrolysis to form a compound in which $OR^2$ represents hydroxyl;
(c) esterification of a compound in which $OR^2$ represents hydroxyl to form a compound in which $OR^2$ represents on esterified hydroxyl group;
(d) transesterification of a compound in which $OR^2$ represents an esterified hydroxyl group.

2. A method according to claim 1 wherein the photochemical reaction is carried out by irradiating with UV light of wavelength from 300 to 370 nm, preferably 330 nm.

3. A method according to claim 1 wherein prior to step (a) a compound of formula (VIII) in which $OR^3$ is an esterified hydroxyl group is isolated at a temperature below 0° C. by neutralisation with base, dilution with water and solvent extraction.

4. A method according to claim 3 characterised in that the compound of formula (VIII) is isolated at temperatures below −10° C.

5. A method according to claim 1 wherein step (a) is carried out by contacting a resulting compound of formula (VIII) with methyl iodide and potassium in liquid ammonia.

6. A method according to claim 1 in which $R^2$ and $R^3$ represents alkyl- or aryl-sulphonyl groups or R—CO radicals in which R represents an unsubstituted or halogen-substituted alkyl, aryl or alkaryl group.

7. A method according to claim 1 characterised in that the photochemical reaction is carried out at a temperature between −10° and −30° C.

8. A method according to claim 1 characterised in that the concentration of $H_2SO_4$ in methanol is from 2 to 10% w/v.

9. A method according to claim 1 characterised in that the transesterification is carried out using alkali-metal carboxylates in dimethyl formamide or dimethyl sulphoxide.

10. A method according to claim 1 characterised in that $R^3$ represents methane-sulphonyl.

11. A method according to claim 1 characterised in that $R^2$ represents 5-bromo-nicotinoyl.

* * * * *